United States Patent [19]

Tustin

[11] Patent Number: 4,788,356
[45] Date of Patent: Nov. 29, 1988

[54] NOVEL METHOD FOR OXYIODINATION PRODUCT PARTIAL PURIFICATION

[75] Inventor: Gerald C. Tustin, Kingsport, Tenn.

[73] Assignee: Eastman Kodak Company, Rochester, N.Y.

[21] Appl. No.: 109,030

[22] Filed: Oct. 16, 1987

[51] Int. Cl.[4] ............... C07C 17/152; C07C 17/15
[52] U.S. Cl. .................................. 570/203; 570/208
[58] Field of Search ............. 570/203, 206, 208, 211

[56] References Cited

U.S. PATENT DOCUMENTS

| | | | |
|---|---|---|---|
| 3,363,010 | 1/1968 | Schwarzenbek | 570/203 |
| 3,544,542 | 2/1971 | Prah et al. | 570/203 |
| 3,600,331 | 8/1971 | Ingwalson | 570/203 |
| 4,240,987 | 12/1980 | Martin et al. | 570/206 |
| 4,391,785 | 7/1983 | Rosinki et al. | 502/77 |
| 4,513,092 | 4/1985 | Chu et al. | 502/77 |
| 4,605,799 | 8/1986 | Kishio | 570/211 |

FOREIGN PATENT DOCUMENTS

| | | | |
|---|---|---|---|
| 0181790 | 5/1986 | European Pat. Off. | 570/206 |
| 183579 | 6/1986 | European Pat. Off. | 570/203 |
| 0077631 | 5/1982 | Japan | 570/206 |
| 58-7830 | 5/1983 | Japan . | |
| 59-219241 | 12/1984 | Japan . | |
| 159496 | 3/1964 | U.S.S.R. | 570/206 |
| 453392 | 1/1975 | U.S.S.R. . | |

OTHER PUBLICATIONS

Groggins, "Unit Processes in Organic Chemistry", Fifth Ed. (1958) McGraw-Hill Book Co., Inc. p. 262.

Primary Examiner—Werren B. Lone
Attorney, Agent, or Firm—Charles R. Martin; William P. Heath

[57] ABSTRACT

A process for iodinating aromatic compounds, comprising the steps of iodinating an aromatic compound, separating a desired iodoaromatic product from the product mixture, purifying said desired iodoaromatic product, and isolating said desired product.

6 Claims, 2 Drawing Sheets

NOVEL METHOD FOR OXYIODINATION PRODUCT PARTIAL PURIFICATION

BACKGROUND OF THE INVENTION

1. Field of the Invention

The present invention relates to processes for iodinating aromatic compounds and to processes for partially separating the reaction products.

2. Discussion of the Background

It has long been desired to be able to derivitize aromatic compounds and in particular condensed ring aromatic compounds in commercially attractive quantities since many of these compounds possess properties which would fill long-sought needs. In particular, substituted benzene and naphthalene carboxylic acids or esters are particularly desired for use in the manufacture of polyesters which would have excellent properties when fabricated into films, bottles or coatings. However, techniques for producing these carboxylic acids and esters are very expensive and impractical for commercial exploitation.

Also commercially important are poly(arylene sulfide) resins which are thermosetting-thermoplastic polymer materials with good thermal stability, unusual insolubility, resistance to chemical environments and inherent flame resistance. Poly(arylene sulfide) resins are useful for applications such as coatings for pipes, tanks, pumps and other equipment.

Halogenated aromatic compounds provide a convenient feedstock material for the preparation of both aromatic polyesters and poly(arylene sulfide) resins. Iodoaromatic compounds, and in particular, monoiodoaromatic and diiodoaromatic compounds provide a common starting material from which to produce polyesters and poly(arylene sulfide) resins.

Synthesis of iodobenzene starting from benzene and iodine is usually carried out in the liquid phase in the presence of an oxidative agent, preferably nitric acid. Such techniques have been described in the literature and in particular in Japanese No. 58/77830, U.S.S.R. Patent No. 453392 by Data and Chatterjee in the *Journal of the American Chemical Society*, 39, 437 (1917). Other oxidative agents have also been suggested but none of these have proven to be more efficient or convenient than nitric acid. Typical of the other oxidative agents which have been suggested are iodic acid, sulfur trioxide and hydrogen peroxide as described by Butler in the *Journal of Chemical Education*, 48, 508 (1971). The use of metal halogenides to catalyze iodination has been suggested by Uemura, Noe, and Okano in the *Bulletin of Chemical Society of Japan*, 47, 147 (1974). The concept of direct iodination of benzene in the gas phase over a 13X zeolite has been suggested in Japanese Patent Publication No. 82/77631 in the absence of any oxidizing agent.

Ishida and Chono in Japanese Kokai No. 59/219241 have suggested a technique for oxyiodinating benzene over very acidic zeolite catalysts having a silica to alumina ($SiO_2:Al_2O_3$) ratio of greater than 10. In this technique benzene is reacted with iodine in the presence of oxygen to produce iodinated benzene. According to this disclosure approximately 96% of the benzene which is converted is converted to the iodinated form. However, the remaining benzene is oxidized to carbon dioxide and other combustion products resulting in the loss of valuable starting material.

Paparatto and Saetti disclosed in European Patent Application Nos. 181,790 and 183,579 techniqes for oxyiodination of benzene over zeolite catalysts. European Patent Application No. 181,790 suggests the use of ZSM-5 and ZSM-11 type zeolites which have been exchanged prior to use with the least one bivalent or trivalent cation. According to this disclosure the utilization of these zeolites in the acid or alkaline form results in a rapid decrease in catalytic activity in relatively few hours.

European Patent Application No. 183,579 suggests the utilization of X type or Y type of zeolite in non-acid form. According to No. 183,579 the X or Y zeolites have to be used in the form exchanged with monovalent, bivalent or trivalent cations and in particular with alkaline or rare earth cations. The techniques of Nos. 181,790 and 183,579 prepare the monoiodobenzene in selectivities in excess of 90% and only distinctly minor amounts of the diiodobenzene compounds.

Accordingly, a need exists for a process which can iodinate aromatic compounds at high conversions.

A further need exists for a process which is flexible enough to allow for the production of iodoaromatic compounds and yet is is economical and practical for commercial use.

SUMMARY OF THE INVENTION

Accordingly one object of the present invention is to provide a process for iodinating aromatic compounds and partially separating the reaction products.

Another object is to provide an iodination process in which the partially purified products can be recycled to conserve reaction materials.

These and other objects of the present invention which will become apparent from the following specification have been attained by the present process which comprises (1) iodinating an aromatic compound, (2) separating the product mixture into two portions, a portion enriched in the desired iodoaromatic product and a portion depleted of said desired iodoaromatic product, and (3) recovering said desired iodoaromatic product from said enriched portion.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
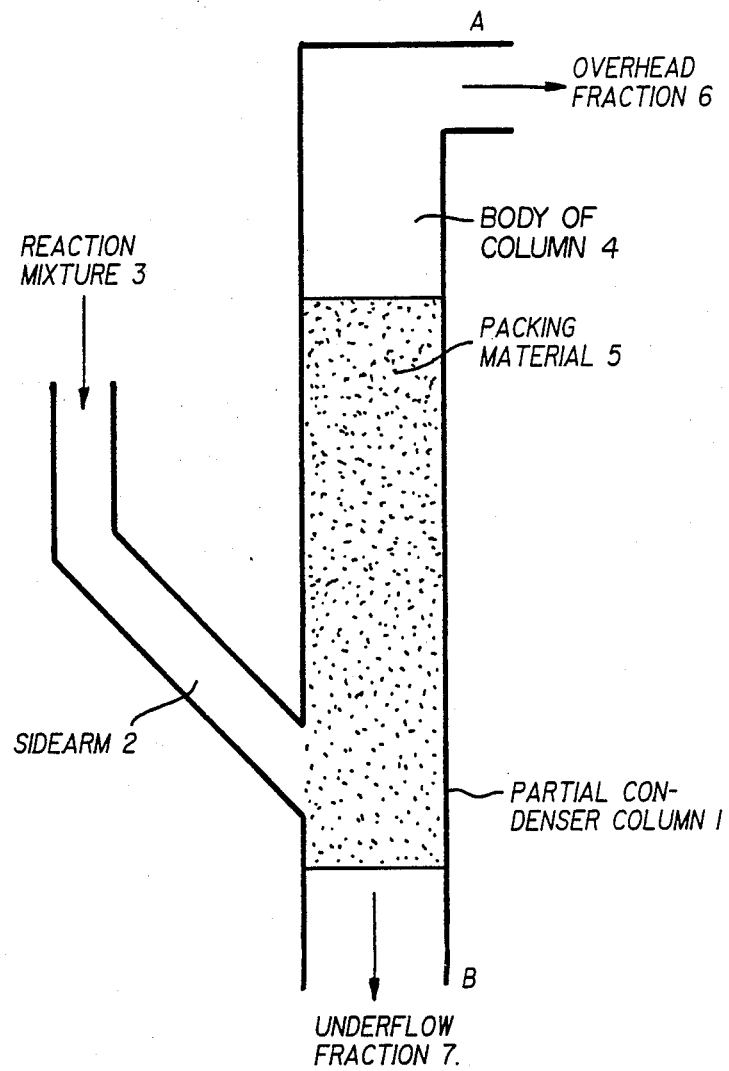
FIG. 1 is a diagram of a partial condenser column.

Aromatic compounds which can be iodinated according to the process of the present invention are essentially any aromatic compound including substituted and unsubstitued aromatics. Suitable aromatic compounds include hydrocarbon aromatics, nitrogen-containing aromatics, oxygen-containing aromatics and sulfur-containing aromatics. Typical hydrocarbon aromatics include benzene and biphenyl, and condensed ring aromatics such as naphthalene and anthracene. Suitable sulfur-containing aromatics include thiophene and benzothiophene. Typical nitrogen-containing aromatics include pyridine and benzopyridine and typical oxygen-containing aromatics include compounds such as furan and benzofuran. Additionally, substituted aromatics including diaryl sulfones, diarylethers, diarylcarbonyls, diarylsulfides and the like may be iodinated. The aromatic compounds may be substituted by alkyl groups, preferably alkyl groups having from 1–10 carbon atoms if the specific iodination process which is utilized can tolerate the presence of alkyl substituents without substantial oxidation of the alkyl groups. Especially preferred alkyl groups are methyl, ethyl, propyl, and butyl groups.

Additional substituents on the aromatic compounds may include phenyl, halogen, hydroxy, nitro, amino, alkoxy, carboxylate and carboxylic acid substituents as well as aryl sulfones and aryl ketones.

The aromatic compounds may be iodinated by any suitable iodination process. The particular iodination process which is selected will depend on the identity of the starting materials and the desired product to be formed. The iodination reaction may be either gas phase or liquid phase. Suitable liquid phase reactions are generally carried out in the presence of oxidizing agents although the iodination process of the present invention is not limited to these processes. Typical oxidizing agents include iodic acid, sulfur trioxide and hydrogen peroxide as well as nitric acid as described above. Alternatively, the iodination reaction can be conducted in the gas phase with or without the use of a catalyst. While any iodination process may be used to iodinate the aromatic compound, it is preferred that the iodination reaction be an oxyiodination reaction conducted in the gas or liquid phase. Especially preferred oxyiodination reactions are those described in detail in copending application Ser. Nos. 06/912,806, filed Sept. 9, 1986; 07/029,896, filed Mar. 25, 1987; 07/029,959, filed Mar. 25, 1987; 07/029,897, filed Mar. 25, 1987; 07/029,898, filed Mar. 25, 1987; 07/110,737 filed July 6, 1987. The disclosures of these copending applications are incorporated herein by reference for a more complete description of these oxyiodination reactions and the catalysts which are used in these processes.

Typical iodinated aromatic products which are produced by these iodination processes include iodobenzenes, iodonaphthalenes, as well as iodinated heteroaromatic compounds. Of particular commercial interest are the iodobenzenes and iodonaphthalenes since these iodoaromatic compounds can be further processed to produce polyesters and poly(arylene sulfide) resins. Especially preferred products are monoiodobenzenes, diiodobenzenes, monoiodonaphthalenes and diiodonaphthalenes, with para-diiodobenzene and 2,6-diiodonaphthalene being very especially preferred. Although any of these preferred products may be produced by the iodination reaction of the present process, the invention will now be further disclosed with reference to 2,6-diiodonaphthalene. It should be understood that any of the products noted above are within the scope of the invention.

The separation and concentration of the desired reaction product, i.e., 2,6-diiodonaphthalene, from the reaction mixture resulting from the iodination reaction can be accomplished by crystallization, a partial condenser column, or other suitable means for removing unreacted starting material, iodine, water and low molecular weight side products from the reaction mixture. It is especially preferred that the iodine and water be removed from the reaction mixture since water and particularly iodine are corrosive to downstream processing equipment. The removal of these compounds from the reaction mixture enables one to use lower priced materials in constructing the downstream processing equipment. The removal of iodine from the product mixture prevents the contamination of the crystallization unit or adsorption/desorption unit discussed below. Additionally, the separation step allows one to remove lower molecular weight side products and recycle these as well as unreacted naphthalene and iodine to the iodination reaction.

The remaining reaction mixture will contain the desired monoiodoaromatic and diiodoaromatic compounds as well as higher iodinated products. In this manner, the partial separation reduces the product mixture volume resulting in a further cost saving since downstream processing equipment is only required to handle smaller volumes of materials.

A preferred method of accomplishing the separation of the reaction products is the use of a partial condenser column such as that shown in FIG. 1. The partial condenser (1) is generally constructed of glass, or Hastalloy. In its simplest form, the partial condenser has a side arm (2) through which the reaction mixture (3) is charged to the partial condenser. The reaction mixture is partially separated on the body of the column (4) which may be optionally packed with conventional inert packing materials (5) to improve the efficiency of the separation. The overhead fraction exiting from the top of the body (6) of the partial condenser contains lower boiling materials while the underflow existing from the bottom of the body of the column will contain higher boiling point materials including the desired diiodoaromatic compounds. In general, unreacted naphthalene, iodine, water and low boiling point organic compounds will be present in the overhead fraction. The underflow fraction (7) will contain diiodoaromatic and triiodoaromatic compounds as well as higher iodinated compounds and is passed to further downstream processing equipment.

The partial condenser is particularly effective in providing a partial separation of the reaction mixture and in its simplest form does not require the addition of external heat or cooling means. However, by providing the partial condenser with a heat transfer means, it is possible to remove heat from an exothermic iodination reaction and use this heat to perform useful work such as the generation of high pressure steam, preheat reactants and the like, to reduce overall energy consumption. In this embodiment, the partial condenser serves to both separate and cool the reaction mixture. As noted above, the reaction mixture is partially separated reducing the volume of the reaction mixture which must be handled by downstream processing equipment. This is possible since the partial condenser does not require the use of solvents and in fact is operated such that no solvents need be added or removed during its operation. The partial condenser may be provided with a heating means to uniformly heat the condenser or to supply a heating or cooling gradient in the condenser. In this manner, the partial condenser can be operated at temperatures either lower or higher than the reaction mixture exiting from the iodination reaction. The exact temperature at which the partial condenser is operated will depend on engineering conditions, the particular iodination reaction which is performed and the degree of separation which is desired. Generally, when performing a naphthalene oxyiodination reaction the reaction mixture has a temperature of approximately 300°-400° C. The partial condenser is generally maintained at a much lower temperature, typically between about 150°-250° C., preferably 180°-220° C. However, higher or lower temperatures are possible depending on the desired separation.

Additionally, the performance of the partial condenser can be improved by including additional features such as (a) providing a current of hot gas injected into the bottom of the condenser, (b) adding a zone to allow for variable degrees of reflux within the column, and (c) refining the design to increase the number of stages and optimize the location of the side arm entry point on the condenser. The optimization of these design characteristics is within the ability of one skilled in the art.

The overhead stream from the partial condenser typically contains water which is optionally removed before the overhead stream is recycled to an oxyiodination reaction. Known dehydration or water removal process may be used to remove water.

Figure 2:
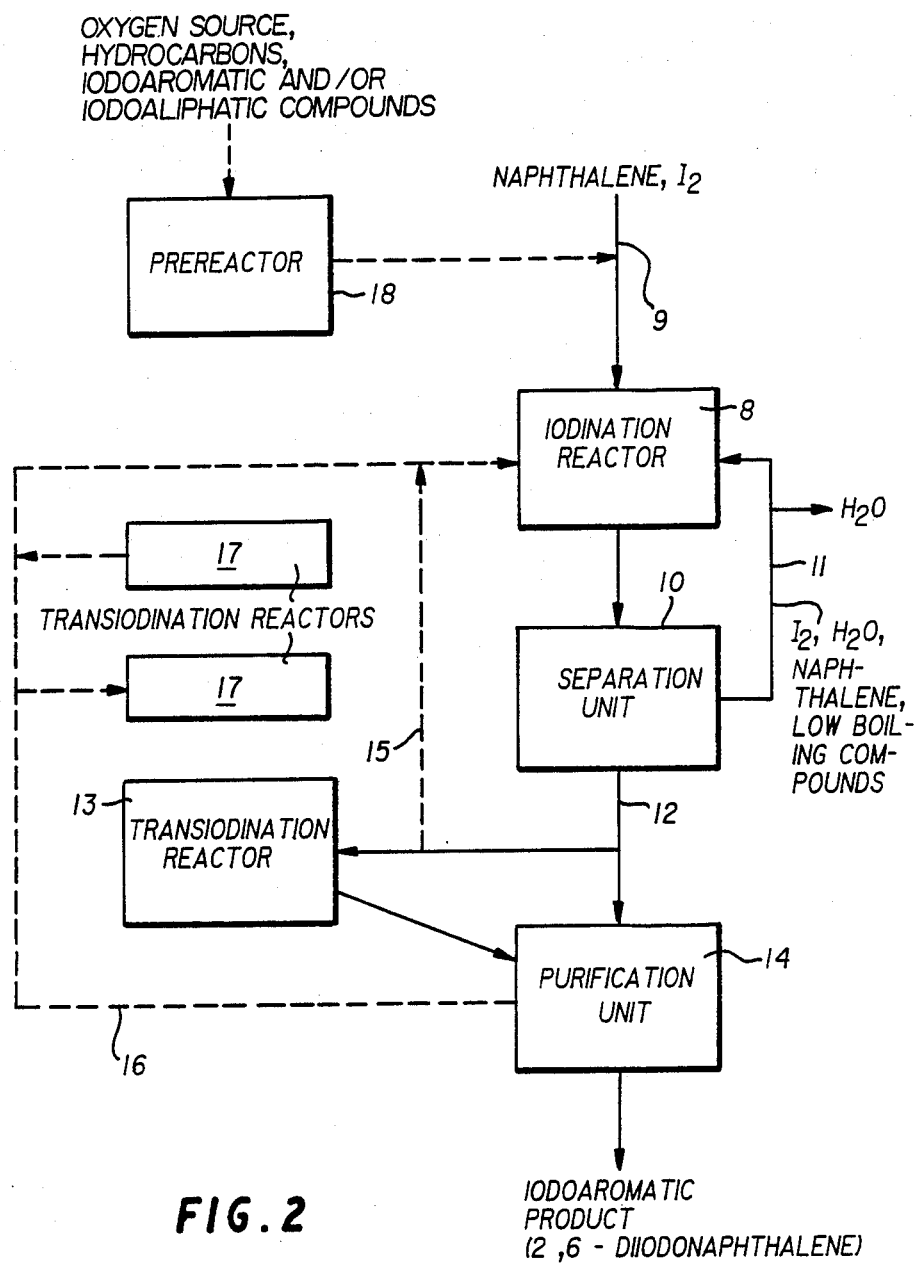
FIG. 2 shows a block diagram illustrating the unit operations of the present iodination process.

Further downstream processing options for the underflow stream are shown in FIG. 2. When one desires to produce 2,6-diiodonaphthalene, iodine and naphthalene feedstocks are fed to the iodination reactor (8) by means of one or more feedlines (9). The product reaction mixture is then passed to a separation unit (10) such as, for example the partial condenser column for separation into a portion which is enriched in the desired product, i.e., 2,6-diidoonapthalene, and a portion which is depleted in 2,6-diiodonaphthalene. After separation, iodine, unreacted starting material, water and low boiling products can be recycled to the iodination reactor by means of line (11).

The underflow (12) containing the desired 2,6-diiodonaphthalene and higher boiling products can then be directly purified by crystallization or other suitable processes to obtain pure 2,6-diiodonaphthalene or can be passed to a transiodination reactor (13) to redistribute iodine among the product compounds and thereby optimize the content of 2,6-diiodonaphthalene. While any suitable transiodination process may be used, the preferred transiodination processes are those disclosed in copending application Ser. Nos. 07/029,899, filed Mar. 25, 1987; 07/029,956, filed Mar. 25, 1987 and 07/029,949, filed Mar. 25, 1987. The disclosures of these copending applications are incorporated herein by reference to provide a more complete description of these transiodination processes and catalysts.

The transiodination reaction is generally performed to increase the concentration of the desired iodoaromatic compound in the product mixture exiting the partial condenser. If the product mixture contains a sufficiently high concentration of the desired product, for example 2,6-diiodonaphthalene, the underflow can be passed directly to a purification unit (14).

Any process which is capable of purifying 2,6-diiodonaphthalene or any other desired iodoaromatic product, such as para-diiodobenzene, fromo the underflow reaction mixture may be used as the purification step in the present process. Particularly preferred are crystallization processes and the use of adsorption/desorption processes such as those described in copending application Ser. No. 07/110,737, filed July 28, 1987. The disclosure of this copending application is incorporated herein by reference. The purified product is isolated and may then be passed to further downstream processing.

The desired iodoaromatic compound can be isolated by direct melt crystallization or from a suitable solvent. For example, the melt crystallization of 2,6-diiodonaphthalene is accomplished by holding the molten column underflow material at 80° C. until crystallization is complete and then filtering the material at 70°-80° C. 2,6-diiodonaphthalene may also be recovered from the column underflow material by solvent crystallization from hot benzene, toluene, xylenes, naphthalene, aliphatic hydrocarbons, halogenated organic molecules (including other iodoaromatic compounds) and mixtures thereof. Additional purification of the isolated crystals is accomplished by a solvent wash.

For iodoaromatic products which are predominantly or selectively produced, it is not necessary to use a transiodination reactor. For example, para-diiodobenzene is produced in high yield from the iodination of benzene and may be purified directly. If the particular iodination reaction is very selective, a purification unit may not be necessary and the underflow from the separation unit, i.e., the partial condenser column, may be passed directly to further downstream processing. For example, in the production of para-diiodobenzene, the underflow from the partial condensor column may be passed directly to a carbonylation reactor to form terephthalate esters without an intermediate purification process. The terephthalate ester may be then separated from the remaining reaction products at this stage. The direct downstream processing of the underflow from the partial condenser column may also be employed when producing 2,6-diiodonaphthalene. When a mixture of 2,6- and 2,7-diiodonaphthalenes is formed in the iodination reactor they may then be separated in an adsorption/desorption unit such as that noted above. However, if desired, the 2,6/2,7 mixture may be passed to downstream processing such as a carbonylation reactor to produce the 2,6 and 2,7-naphthalene diesters. The 2,6 and 2,7-diesters may then be separated at this stage.

The present process allows for many options in the recycling of unreacted starting materials, iodine and iodinated aromatic compounds to the iodination reaction. For example, instead of going to a transiodination reactor (13) or to a purification unit (14), a portion of the underflow from the partial condenser may be directly recycled via line 15 to the iodination reactor (oxyiodination) to increase product yield. In another embodiment, the undesired products resulting from the adsorption/desorption unit or the crystallization unit (purification unit) can be passed directly to the oxyiodination reactor (8) via line 16 or may be passed through one or more transiodination reactors (17) to adjust the product composition before recycling to the oxyiodination reactor. this embodiment is the most economical since it results in the lowest losses of iodine and naphthalene. It is to be understood that one or more recycle streams may be passed to the oxyiodination reaction simultaneously.

In a further embodiment, a prereactor (18) may be placed upstream from the iodination reactor when the reactor is an oxyiodination reactor. A prereactor such as that disclosed in copending application Ser. No. 07/82,303, filed July 28, 1987 combusts hydrocarbons, iodoaromatic compounds and/or iodoaliphatic compounds to produce molecular iodine which is then passed to the oxyiodination reactor. Preferably, hydrocarbon and iodoaromatic compounds which do not transiodinate are fed to the prereactor to recover iodine and reduce the amount of undesired waste materials. In general, it is less economical to pass the underflow from the partial condenser or the undesired materials from the purification unit to the prereactor since this results in an unnecessary loss of aromatic compounds by combustion. The prereactor is an effective means of recycling iodine to the oxyiodination reaction, however.

Other features of the invention will become apparent during the course of the following descriptions of exemplary embodiments which are given for illustration of the invention and are not intended to be limiting thereof.

EXAMPLES

All of the examples illustrate naphthalene oxyiodination. The partial condenser column is shown in FIG. 1. The principles apply to the separation of products from the oxyiodination of other aromatic compounds as well.

The catalyst used in the examples is ⅛ inch 13X zeolite extrudates that have been exchanged four times with potassium chloride. The same catalyst charge is used in all of the examples. A one-inch O.D. Vycor tube fitted with a thermocouple well is loaded with three inches of Vycor chips as a supporting material, eight inches of catalyst (67 mL), and 11 inches of Vycor chips as a preheat zone. A thermocouple is located one inch into the catalyst bed from the top of the bed. Naphthalene and iodine are fed from separate vaporizers held at 179°–180° C. and 120° C., respectively, by passage of separate air streams of known flow rate through the vaporizers. The balance of the air flow is provided by a third air stream of known flow rate. The catalyst is heated in an electric furnace and the material exiting the reactor is fed directly into the inlet of the partial condenser shown in the figure. The partial condenser is maintained at the temperature specified in each example. Condensed product exiting the bottom of the partial condenser at B is collected in a tared flask. Product exiting the top of the partial condenser at A is collected in a tared vented bottle. Products are weighed, dissolved in toluene and analyzed by gas chromatography for organic products and by thiosulfate titration for iodine.

Example 1

This example illustrates the operation of the partial condenser at 180° C. with reactants at low space velocity. The conditions and results are detailed in Table 1.

Example 2

Example 1 is repeated with the partial condenser at 200° C. with essentially the same space velocity. The conditions and results are detailed in Table 1.

Example 3

Example 1 is repeated with the partial condenser at 220° C. with essentially the same space velocity. The conditions and results are detailed in Table 1.

Example 4

Example 2 is repeated at the same temperature but at higher space velocity. The conditions and results are detailed in Table 1.

Example 5

This example illustrates the low corrosiveness of the enriched product exiting the bottom of the partial condenser. A 168 g sample of the product exiting the bottom of the partial condenser is dissolved in 1500 mL hot p-xylene to simulate downstream processing. The mix is divided into six portions and each portion is refluxed 237 hours in the presence of coupons made from the materials shown in Table 2. The data from Table 2 illustrate that the corrosion of all materials examined is negligible. Thus, the processing equipment downstream from the bottom of the partial condenser can be made of inexpensive materials such as for example, 304 stainless steel.

TABLE 1

Naphthalene Oxyiodination Using Partial Condenser

| Example Number | 1 | | 2 | | 3 | | 4 | |
|---|---|---|---|---|---|---|---|---|
| Partial Condenser Temp, °C. | 180 | | 200 | | 220 | | 200 | |
| Space Velocity, $gl^{-1} hr^{-1}$ | 620 | | 640 | | 620 | | 1160 | |
| Molar Feed Ratio: $Naph/I_2/O_2$ | 2.0/1.0/2.2 | | 2.0/1.0/2.2 | | 2.0/1.0/2.2 | | 2.2/1.0/2.2 | |
| Reactants Fed, g | 29.07 | | 53.04 | | 29.72 | | 59.25 | |
| Total Products Isolated, g | 29.63 | | 51.72 | | 29.53 | | 63.14 | |
| Section where product collected | Top (A) | Bottom (B) | Top (A) | Bottom (B) | Top (A) | Bottom (B) | Top (A) | Bottom (B) |
| Split Products Isolated, g | 6.67 | 22.96 | 14.69 | 37.03 | 10.35 | 19.18 | 20.04 | 43.10 |
| $I_2$, g | 0.08 | 0.17 | 0.13 | 0.13 | 0.13 | 0.04 | 0.73 | 0.15 |
| $I_2$, wt % | 1.28 | 0.75 | 0.92 | 0.36 | 1.28 | 0.22 | 3.74 | 0.34 |
| Naphthalene | 72.0 | 8.6 | 56.0 | 4.3 | 55.7 | 3.7 | 69.7 | 8.3 |
| 2-Iodonaphthalene* | 19.1 | 39.4 | 30.9 | 36.2 | 30.0 | 34.9 | 21.5 | 38.9 |
| 1-Iodonaphthalene* | 7.2 | 14.0 | 10.6 | 13.1 | 10.8 | 11.9 | 7.5 | 14.0 |
| Other Diiodonaphthalenes* | 0.2 | 6.6 | 0.5 | 8.3 | 0.7 | 8.1 | 0.3 | 6.3 |
| 2,6 + 2,7-Diidonaphthalenes* | 1.2 | 31.3 | 1.8 | 33.9 | 2.6 | 37.6 | 1.0 | 30.0 |

Conditions: K-X zeolite catalyst at 320° C.
*Values given as area %

TABLE 2

| | Corrosion Studies on p-Xylene Solutions of Partially Condensed Product | | | | | |
|---|---|---|---|---|---|---|
| | Corrosion | Degree of Attack* | | | | Exposure |
| Material Mark | Rate (MFY)** | Gen'l | Bitting | SCC | Temp. | Time (Hours) |
| 316L SS 3 | 0.3 | A | A | A | 138° C. | 237 |

TABLE 2-continued

Corrosion Studies on p-Xylene Solutions of Partially Condensed Product

| Material Mark | Corrosion Rate (MFY)** | Degree of Attack* | | | Temp. | Exposure Time (Hours) |
| --- | --- | --- | --- | --- | --- | --- |
| | | Gen'l | Bit-ting | SCC | | |
| 304 SS 11 | 0.3 | A | A | A | 138° C. | 237 |
| CAR 20DB 12 | 0.2 | A | A | A | 138° C. | 237 |
| 904L SS 4 | 0.2 | A | A | A | 138° C. | 237 |
| HAST G 5 | 0.4 | A | A | A | 138° C. | 237 |
| HAS C276 4 | 0.1 | A | A | A | 138° C. | 237 |

*A = NIL
B = Mild
C = Medium
D = Severe
**MPY = Mils per year (.001 inches/year)

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for the preparation of an iodoaromatic compound selected from the group consisting of diiodobenzene, diiodonaphthalene or diiododiphenyl comprising the steps of (1) reacting benzene, naphthalene or biphenyl with oxygen and iodine over a zeolite X catalyst exchanged with potassium, rubidium or cesium ions to produce a product mixture, (2) partially condensing the product mixture in the presence of water into a portion enriched in the iodoaromatic compound and a portion which is depleted in the iodoaromatic compound and contains water, and (3) recovering the iodoaromatic compound from the portion of the product mixture enriched in the iodoaromatic compound.

2. The process of claim 1 wherein the partial condensing step is performed with a condensing column.

3. The process of claim 2 wherein the overhead fraction from the condensing column comprises the portion depleted in the diiodoaromatic compound and the underflow from the condensing column comprises the portion enriched in the diiodoaromatic compound.

4. The process of claim 2 wherein the partial condensing column is operated at a temperature of about 150°-250° C.

5. The process of claim 4 wherein the partial condensing column is operated at a temperature of about 180°-220° C.

6. A process for the preparation of diiodonaphthalene comprising the steps of (1) reacting naphthalene with oxygen and iodine over a zeolite X catalyst exchanged with potassium to produce a product mixture, (2) partially condensing the product mixture in the presence of water into a portion enriched in diiodonaphthalene containing water, and (3) recovering the diiodonaphthalene from the portion of the product mixture enriched in diiodonaphthalene.

* * * * *